(12) United States Patent
Kim et al.

(10) Patent No.: US 9,999,698 B2
(45) Date of Patent: Jun. 19, 2018

(54) OLFACTORY DISPLAY

(71) Applicant: NATIONAL INSTITUTE OF INFORMATION AND COMMUNICATIONS TECHNOLOGY, Koganei-shi, Tokyo (JP)

(72) Inventors: Dong Wook Kim, Koganei (JP); Hiroshi Ando, Koganei (JP)

(73) Assignee: NATIONAL INSTITUTE OF INFORMATION AND COMMUNICATIONS TECHNOLOGY, Koganei-shi (JP)

( * ) Notice: Subject to any disclaimer, the term of this patent is extended or adjusted under 35 U.S.C. 154(b) by 80 days.

(21) Appl. No.: 15/039,251

(22) PCT Filed: Nov. 26, 2014

(86) PCT No.: PCT/JP2014/081155
§ 371 (c)(1),
(2) Date: May 25, 2016

(87) PCT Pub. No.: WO2015/080117
PCT Pub. Date: Jun. 4, 2015

(65) Prior Publication Data
US 2017/0080118 A1 Mar. 23, 2017

(30) Foreign Application Priority Data
Nov. 26, 2013 (JP) .................................. 2013-244225

(51) Int. Cl.
*A61L 9/12* (2006.01)
*B01F 3/04* (2006.01)
*A61L 9/14* (2006.01)

(52) U.S. Cl.
CPC ................. *A61L 9/12* (2013.01); *A61L 9/14* (2013.01); *B01F 3/0407* (2013.01);
(Continued)

(58) Field of Classification Search
CPC .......... A61L 9/12; B01F 3/04; B01F 3/04049; B01F 3/04063; B01F 3/0407; B01F 3/04085
(Continued)

(56) References Cited

U.S. PATENT DOCUMENTS

2013/0327848 A1  12/2013  Kim et al.
2015/0283282 A1  10/2015  Kim et al.

FOREIGN PATENT DOCUMENTS

JP       2003-260121 A       9/2003
JP       2007075578 A  *    3/2007
(Continued)

OTHER PUBLICATIONS

International Search Report dated Feb. 24, 2015, issued in counterpart International Application No. PCT/JP2014/081155 (2 pages).

*Primary Examiner* — Robert A Hopkins
(74) *Attorney, Agent, or Firm* — Westerman, Hattori, Daniels & Adrian, LLP

(57) ABSTRACT

An olfactory display includes a housing and a plurality of fragrance chambers formed in the housing. In each fragrance chamber, a solid-like fragrance source is accommodated and an airflow source is provided to send air into the fragrance chamber from an air intake port. An auxiliary airflow source that emits odorless air is also provided in the housing. The airflow source and the auxiliary airflow source are operated alternately or simultaneously. In response to a user operating an adjustment knob of a controller, operating time periods and stopping time periods of the airflow source and the
(Continued)

auxiliary airflow source are changed, or the number of operating times is changed within a predetermined operating time period. A mixing ratio of the fragrance and the odorless air may also be adjusted by changing a voltage value of an alternating voltage to be applied to a piezoelectric device of the airflow source.

12 Claims, 13 Drawing Sheets

(52) U.S. Cl.
CPC ..... *B01F 3/04085* (2013.01); *A61L 2209/111* (2013.01); *A61L 2209/132* (2013.01)

(58) Field of Classification Search
USPC ........................ 261/26, 30, DIG. 88; 422/124
See application file for complete search history.

(56) References Cited

FOREIGN PATENT DOCUMENTS

| | | | |
|---|---|---|---|
| JP | 2009-82273 | A | 4/2009 |
| JP | 2009-265453 | A | 11/2009 |
| JP | 2012-173381 | A | 9/2012 |
| JP | 5093543 | B1 | 12/2012 |
| JP | 5288573 | B1 | 9/2013 |
| JP | 2013-236241 | A | 11/2013 |

\* cited by examiner

OLFACTORY DISPLAY

TECHNICAL FIELD

The present invention relates to an olfactory display, and more specifically, an olfactory display presenting a fragrance to a user.

BACKGROUND ART

An example of a background art is disclosed in Patent literature 1. A scent generating apparatus disclosed in this Patent literature 1 pulsively injects a fragrance into the flowing air for infinitesimal time at short time intervals.

Furthermore, another example of the background art is disclosed in Patent literature 2. An olfactory display disclosed in this Patent literature 2 controls a concentration of a fragrance component by adjusting a mixing ratio of a fragrance and odorless air.

Patent literature 1: Japanese patent application laying-open No. 2009-82273 [A61M 21/02, A61L 9/02, A45D 34/02]

Patent literature 2: Japanese patent publication No. 5288573 [G09F 9/00, G09F 9/00, A61L 9/12]

SUMMARY OF THE INVENTION

Problem to be Solved by the Invention

However, in Patent literature 1, although the fragrance is pulsively injected for infinitesimal time at short time intervals, since an injected amount is constant, it is impossible to reduce a concentration of the fragrance due to the constant injection amount, and therefore, it is difficult to control a concentration of the fragrance component.

Furthermore, Patent literature 2 fails to disclose a specific method for controlling the concentration of the fragrance component.

Therefore, it is a primary object of the present invention to provide a novel olfactory display.

It is another object of the present invention to provide an olfactory display capable of uniformly presenting a fragrance with a controlled concentration.

Means for Solving the Problem

A first invention is an olfactory display presenting a fragrance, comprising: a housing having an emission port; a fragrance emission portion that is provided in an inside of the housing and configured to emit a fragrance from the emission port; a first air emission portion that is provided in the inside of the housing and configured to emit odorless air from the emission port; and an emission control module configured to make the fragrance emission portion and the first air emission portion operate alternately or simultaneously.

In the first invention, the olfactory display operates in cooperation with an audio-visual display such as a personal computer, television, etc., for example, and presents to a user a fragrance in addition to a content that includes an image and sound. The housing has the emission port, and the fragrance emission portion that emits the fragrance from the emission port is provided in the inside of this housing. Furthermore, the first air emission portion that emits the odorless air from the emission port is provided in the inside of the housing. The emission control module makes the fragrance emission portion and the first air emission portion operate alternately or simultaneously.

According to the first invention, since the fragrance and the odorless air are emitted alternately or simultaneously, it is possible to uniformly present the fragrance with a concentration that is controlled according to a mixing ratio of the fragrance and the odorless air.

A second invention is according to the first invention, wherein the emission control module is configured to change a length of an operating time period that the fragrance emission portion is operated and a length of a stopping time period that the fragrance emission portion is stopped, and a length of an operating time period that the first air emission portion is operated and a length of a stopping time period that the first air emission portion is stopped.

In the second invention, the emission control module makes the fragrance emission portion and the first air emission portion operate alternately, and changes the length of the stopping time period that the first air emission portion is stopped to be made equal to the length of the operating time period that the fragrance emission portion is operated, and changes the length of the operating time period that the first air emission portion is operated to be made equal to the length of the stopping time period that the fragrance emission portion is stopped. Therefore, the mixing ratio of the fragrance and the odorless air is changed.

According to the second invention, it is possible to easily adjust the mixing ratio of the fragrance and the odorless air.

A third invention is according to the first or second invention, wherein the emission control module is configured to change an emission amount of the fragrance during the operating time period that the fragrance emission portion is operated.

In the third invention, the emission control module increases or decreases the emission amount of the fragrance during the operating time period that the fragrance emission portion is operated. Therefore, the mixing ratio of the fragrance and the odorless air can be changed.

According to the third invention, it is also possible to easily adjust the mixing ratio of the fragrance and the odorless air.

A fourth invention is according to any one of the first to the third inventions, and further comprises a second air emission portion that is provided in the inside of the housing and configured to emit odorless air from the emission port, the second air emission portion being different from the first air emission portion, and the emission control module is configured to make the second air emission portion operate together with the first air emission portion.

In the fourth invention, the second air emission portion that is different from the first air emission portion and makes the odorless air emit from the emission port is further provided in the inside of the housing of the olfactory display. The emission control module makes the second air emission portion operate together with the first air emission portion or with being switched from the first air emission portion concerned.

According to the fourth invention, since an amount of the odorless air to be mixed can be changed in a relatively large range, it is possible to control in detail the concentration of the fragrance component.

A fifth invention is according to the first invention, and further comprises a calculation module configured to set the operating time period that the fragrance emission portion is operated to a predetermined time period, and calculate, according to the concentration of the fragrance to be presented, the number of operating times that the fragrance emission portion concerned and the first air emission portion concerned are operated during a fragrance presentation time period that presents the fragrance, and the emission control module is configured to makes the fragrance emission portion and the first air emission portion operate alternately by the number of operating times calculated by the calculation module.

In the fifth invention, the calculation module sets the operating time period that operates the fragrance emission portion to the predetermined time period, and calculates the number of operating times that the fragrance emitting portion concerned and the first air emission portion concerned are operated during the fragrance presentation time period that presents the fragrance according to the concentration of the fragrance to be presented. That is, according to the concentration, the number of operating times for alternately operating the fragrance emission portion and the first air emission portion is calculated. The emission control module makes the fragrance emission portion and the first air emission portion operate alternately only the number of operating times calculated by the calculation module.

According to the fifth invention, it is also possible to uniformly present the fragrance that the concentration is controlled according to the mixing ratio of the fragrance and the odorless air.

A sixth invention is an olfactory display presenting a fragrance, comprising: a housing having a plurality of emission ports that are arranged in positions close to each other; a fragrance emission portion that is provided in an inside of the housing and configured to emit a fragrance from a first emission port out of the plurality of emission ports; a first air emission portion that is provided in the inside of the housing and configured to emit odorless air from a second emission port out of the plurality of emission ports, the second emission port being different from the first emission port; and an emission control module configured to make the fragrance emission portion and the first air emission portion operate alternately or simultaneously.

According to the sixth invention, like the first invention, it is also possible to uniformly present a fragrance that a concentration is controlled according to a mixing ratio of the fragrance and the odorless air.

Advantage of the Invention

According to the present invention, since the fragrance and the odorless air are made to emit alternately or simultaneously, it is possible to uniformly present the fragrance that the concentration is controlled according to the mixing ratio of the fragrance and the odorless air.

The above described objects and other objects, features, aspects and advantages of the present invention will become more apparent from the following detailed description of the present invention when taken in cooperation with the accompanying drawings.

FORMS FOR EMBODYING THE INVENTION

Figure 1:
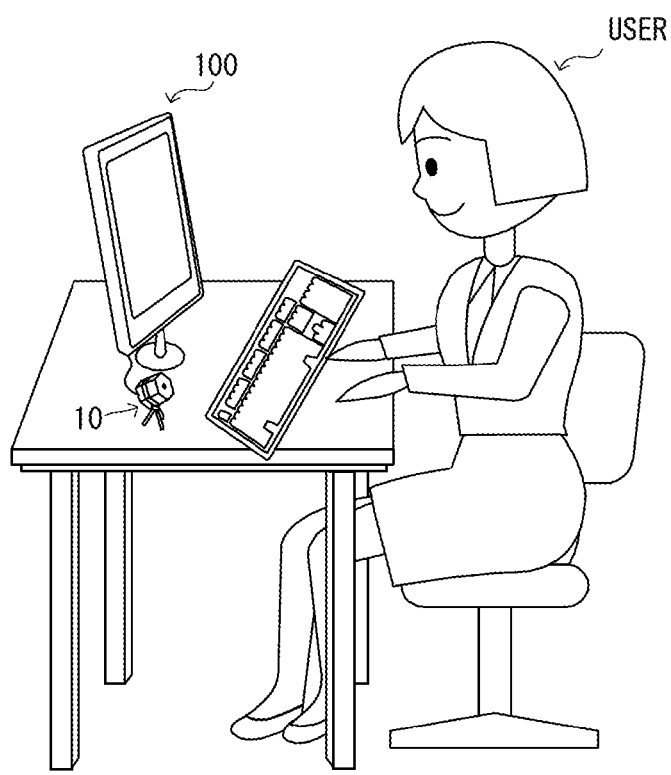
FIG. 1 is an illustration view showing a situation that a fragrance is presented to a user by using an olfactory display that is an embodiment according to the present invention.
Figure 2:
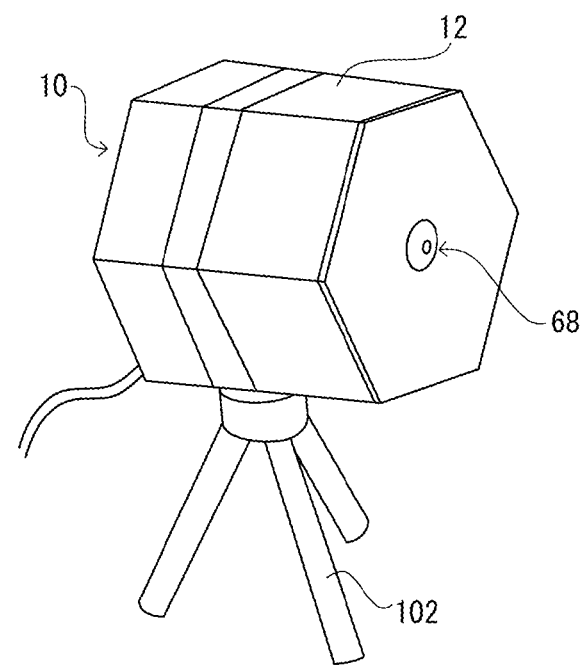
FIG. 2 is an illustration view showing the olfactory display of FIG. 1 in an enlarged manner.

With referring to FIG. 1 and FIG. 2, an olfactory display 10 that is an embodiment according to the present invention is used in order to enhance a reality and a presence of a content by presenting to a user a content including an image and sound while adding a fragrance (olfactory information). The olfactory display 10 presents a fragrance in a time-space-controllable manner, that is, within a range bounded in terms of time and space in cooperation with various kinds of audio-visual displays 100 such as a personal computer, a television, a radio, a game machine, a karaoke machine, a camera, a CD player, a DVD player, a mobile phone, etc., for example.

FIG. 1 and FIG. 2 show, as an example, a situation that the olfactory display 10 is used in cooperation with a host computer such as a personal computer. In this case, the olfactory display 10 is attached to an LCD display, a keyboard or the like such that an emission port 68 that emits a fragrance is turned to a direction of a face of a user, or attached to a tripod 102 or the like to be arranged around the user. Furthermore, a controller 300 (see FIG. 7) is connected to the olfactory display 10, and by turning an adjustment knob 300a provided on the controller 300 left (counterclockwise) or right (clockwise), it is possible to adjust a concentration of a fragrance (fragrance component) to be emitted. However, the controller 300 may be provided, instead of the adjustment knob 300a, with an adjustment button or an adjustment knob having a knob that is made to be slid toward right or left.

Figure 3:
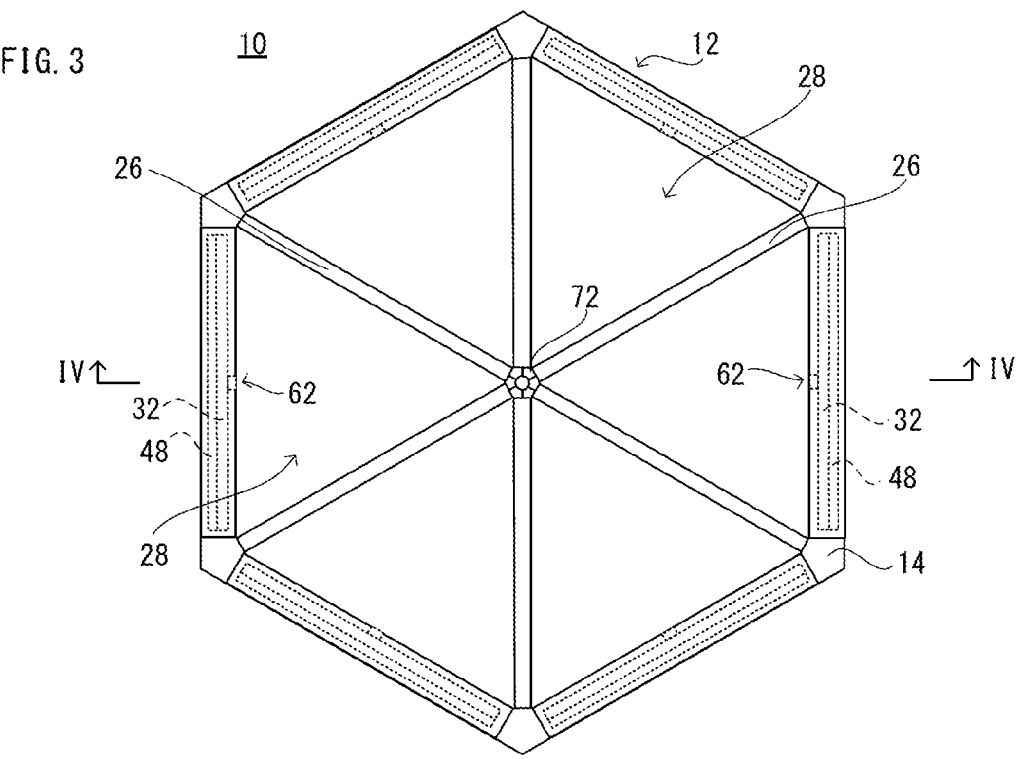
FIG. 3 is an illustration view schematically showing internal structure of the olfactory display of FIG. 1 while viewed from a front direction, and shows a situation of an inside of a housing while omitting a front wall and a fragrance source.

In the following, structure of the olfactory display 10 will be specifically described with reference to FIG. 3 and FIG. 4. FIG. 3 is an illustration view schematically showing internal structure of the olfactory display 10 while viewed from a front direction (user side), and shows an internal situation of a housing 12 provided on the olfactory display 10 while omitting a front wall 16 of the housing 12 and a fragrance source 30. Furthermore, FIG. 4 is a cross-sectional view of the olfactory display 10 that is cut at a line IV-IV in FIG. 3, and schematically shows the internal structure of the olfactory display 10 while viewed from a side direction.

Figure 4:
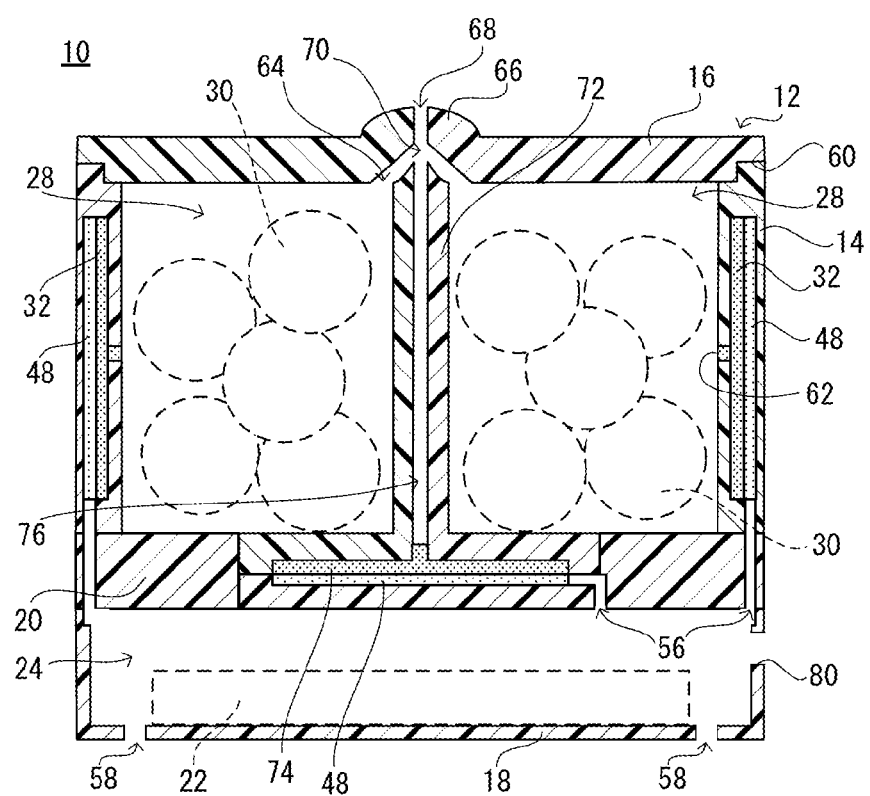
FIG. 4 is a cross-sectional view schematically showing the internal structure of the olfactory display of FIG. 1 while viewed from a side direction, and shows a cross-section being cut at a line Iv-Iv in FIG. 3.

As shown in FIG. 3 and FIG. 4, the olfactory display 10 comprises the housing 12 that constitutes an outer shell, a plurality of fragrance chambers 28, solid-like fragrance sources 30, a plurality of airflow sources 32, an auxiliary airflow source 74, etc.

The housing 12 includes a side wall 14, a front wall 16 and a rear wall 18, and is formed in a shape of a hollow hexagonal prism of proper materials such as an acrylic resin, a fluororesin, a stainless steel, etc. A size of the housing 12 is 60 mm in length between opposite vertex when viewed from a front direction, and 60 mm in length of an axial direction (front-rear direction).

An inside space of the housing 12 is sectioned into a front and a rear with a hexagon plate-like partition wall 20, and a space in a rear side of the partition wall 20 is utilized as a control board room 24 that accommodates a control board 22. The control board 22 has structure that is mounted with electronic components such as a CPU, a memory, etc. on a substrate (see FIG. 7), and connected to the airflow sources 32, the auxiliary airflow source 74, etc. (described later) via wiring (not shown), and controls an operation of the olfactory display 10 concerned.

On the other hand, a space in a front side of the partition wall 20 is sectioned by six (6) partitions 26 that are radially extended when viewed from a front direction, and six (6) fragrance chambers 28 each of which is a closed space having a shape of equilateral triangle prism are formed in the housing 12 while being arranged in a circumference direction. In addition, although the number of the fragrance chambers 28 formed in the housing 12 is not limited especially, when taking miniaturization of the apparatus, an emission performance of the fragrance, etc. into account, it is preferable that the number of the fragrance chambers 28 is set from four (4) to eight (8).

In respective fragrance chambers 28, solid-like fragrance sources 30 having different fragrances are accommodated. The solid-like fragrance source 30 is manufactured by soaking (impregnating) liquid aromatic material into granular porous material, and by making an outer surface and within pores of the porous material hold the liquid aromatic material. For the aromatic material, natural aromatic materials, synthetic aromatic materials and compound aromatic materials thereof are available appropriately. For the porous material, granular body such as calcium silicate, silica gel, rock wool, diatomaceous earth, zeolite, peat, charcoal, vermiculite, bentonite, perlite, carbon nanotube, active carbons, etc. are available appropriately. Although a particle size and shape of the porous material is not limited especially, if taking a passage resistance, etc. within the fragrance chamber 28 into account, it is preferable that the particle size is around 1-6 mm and shape thereof is a globoid. In this embodiment, fifteen (15) fragrance sources 30 that the liquid aromatic material is soaked into the globoid of the calcium silicate having an average particle size of 4 mm are enclosed in each of the fragrance chambers 28. By thus using the solid-like fragrance source 30, it is possible to gradually release the aromatic material (fragrance component) from the fragrance source 30. That is, since the fragrance component can be released for a long period of time, it is possible to use the olfactory display 10 for a long period of time without supplementing the liquid aromatic material into the fragrance source 30 or exchanging the fragrance source 30.

Furthermore, a rectangular plate-like airflow source 32 is provided in each of the fragrance chambers 28. The airflow source 32 is arranged in the side wall 14 such that a nozzle 34 that is provided in a center portion can be communicated with the fragrance chamber 28, and constitutes a part of the side wall 14. Then, the nozzle 34 of the airflow source 32 functions as an air intake port 62 that makes the air flow-in into the fragrance chamber 28. A size of the airflow source 32 is in 20 mm long, 20 mm wide and 2 mm thickness, for example.

Figure 5:
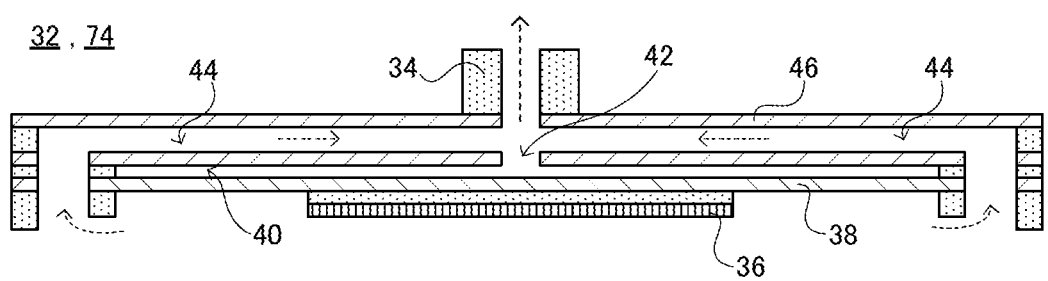
FIG. 5 is a cross-sectional view showing a cross-section when cutting an airflow source provided in the olfactory display of FIG. 1 in a direction of a diagonal line.

FIG. 5 shows a cross-section when cutting the airflow source 32 is cut in a direction of a diagonal line. The airflow source 32 is of a piezoelectric system that comprises a diaphragm 38 that is adhered with a piezoelectric device (piezoelectric element) 36, and by applying an alternating voltage (sign wave voltage or rectangular wave voltage) to the piezoelectric device 36, the diaphragm 38 is bent and vibrated at a high speed in a thickness direction thereof, thereby to generate an airflow.

In the following, an operation of the airflow source 32 will be described briefly. In the airflow source 32, according to high speed vibration of the diaphragm 38 adhered with a disk-like piezoelectric device 36 at approximately 26 kHz, suction and discharge of the air through an air hole 42 that is formed in a center portion of a pump room 40 are repeated. The air that is taken, at the time of suction, into the pump room 40 from a suction passage 44 passes the nozzle 34 that is arranged coaxially with the air hole 42 on a top plate 46 at the time of discharge, and expanded in a tapered pipe within the nozzle 34 to be discharged. At this time, since a negative pressure portion occurs in a space between the air hole 42 and the nozzle 34 due to a venture effect, the air in the suction passage 44 is continuously sucked. Accordingly, a continuous pump operation toward the nozzle 34 from the suction passage 44 can be obtained.

The airflow source 32 (airflow source of the piezoelectric system) thus driven by the piezoelectric device 36 does not have a rotation mechanism such as a blower fan or a scroll blower, and thus, can be reduced in a size and a height, and further consumption electricity is also small. In addition, such the airflow source is of no vibration essentially and has a feature that a higher static pressure can be produced within a short period of time. For such an airflow source 32, a micro blower (type number: MZBX001) manufactured by Murata Manufacturing Co., Ltd, for example, is available.

Furthermore, in the rear side of the airflow source 32 (an upstream side of the air passage), an operation noise suppressing portion 48 for suppressing a leakage of an operation noise of the airflow source 32 (a vibration noise of the diaphragm 38) to an outside is provided. This operation noise suppressing portion 48 is also arranged in the side wall 14, and constitutes a part of the side wall 14. The operation noise suppressing portion 48 is made of suitable materials such as an acrylic resin, a fluororesin, a stainless steel, etc., and formed with a cavity portion in the rear side of the diaphragm 38. A size of the operation noise suppressing portion 48 is in 20 mm long, 20 mm wide and 2 mm thickness, for example.

Figure 6:
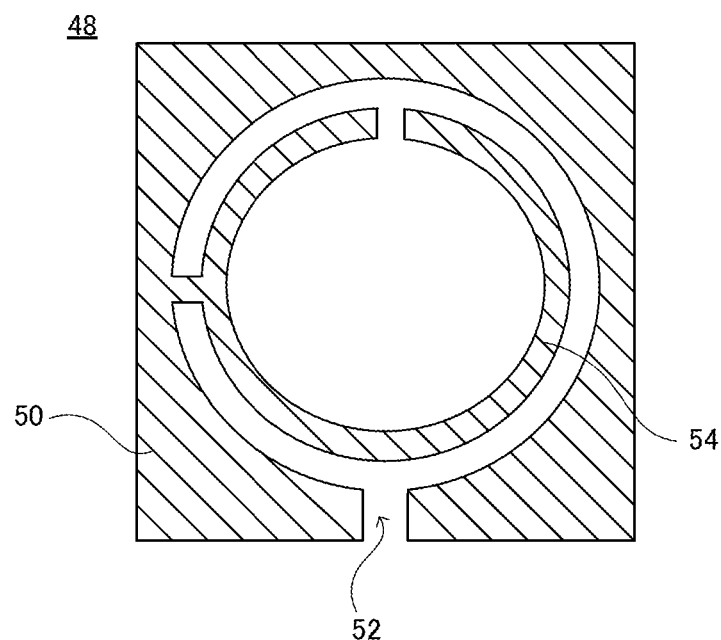
FIG. 6 is a cross-sectional view showing a cross-section when cutting an operation noise suppressing portion provided in the olfactory display of FIG. 1 in a direction intersecting a thickness direction perpendicularly.

FIG. 6 shows a cross-section when cutting the operation noise suppressing portion 48 in a direction intersecting a thickness direction perpendicularly. As shown in FIG. 6, an outside air inlet 52 for sucking-in outside air at the time that the airflow source 32 is operated is formed on a side wall 50 of the operation noise suppressing portion 48, and an inside of the operation noise suppressing portion 48 is partitioned by a C-letter shaped partitioning wall 54. Accordingly, since the operation noise of the airflow source 32 reaches the outside air inlet 52 with making a detour through a maze-like air passage, the leakage of the operation noise from the outside air inlet 52 (and thus an outside air suction port 58) can be suppressed. By providing such an operation noise suppressing portion 48, it is possible to present a fragrance to the user without giving to the user an uncomfortable feeling due to the operation noise. It should be noted that internal structure of the operation noise suppressing portion 48 is not limited to a manner shown in FIG. 6. For example, it may be a mere cavity with no partitioning wall 54 or may be provided with a partitioning wall having another shape.

In addition, the outside air inlet 52 of the operation noise suppressing portion 48 is communicated with the outside of the housing 12 via an air passage 56 that is formed in the side wall 14, the control board room 24 and the outside air suction port 58 that is formed in the rear wall 18 (see FIG. 4). By thus sucking the outside air into the airflow source 32 via the control board room 24, the air in the control board room 24 comes to be always replaced with the outside air during the operation of the airflow source 32. Accordingly, it is possible to radiate the heat rises from the control board 22 adequately.

Returning to FIG. 4, fitting portions 60 that fit with each other are formed in a side edge portion of the front wall 16 of the housing 12 and a front end portion of the side wall 14 of the housing 12, and the front wall 16 is made attachable or detachable to or from the side wall 14. That is, the front wall 16 functions as a lid body that seals a front end opening of the housing 12 (side wall 14) to be openable or closable. The front end opening of the housing 12 when removing the front wall 16 is utilized in order to put the fragrance source 30 in each fragrance chamber 28 or to take out the fragrance source 30 from each fragrance chamber 28.

Furthermore, the air intake port 62 and a fragrance outlet 64 are formed in each fragrance chamber 28. As mentioned above, the nozzle 34 of the airflow source 32 functions as the air intake port 62, and each of the air intake ports 62 is formed at a side of the side wall 14. Furthermore, each of the fragrance outlets 64 is formed at an inner most position in a side of the front wall 16 such that a distance with the emission port 68 becomes short. A diameter of the air intake port 62 and a diameter of the fragrance outlet 64 are 0.8 mm, respectively, for example.

A hemispherical projection portion 66 is provided in a center portion of the front wall 16, and the emission port 68 is formed in a tip end portion of this projection portion 66. A diameter of the emission port 68 is 0.8 mm, for example. Furthermore, the front wall 16 is formed with a fragrance passage 70 that extends in a thickness direction of the front wall 16 so as to penetrate a center portion of the projection portion 66, and makes the emission port 68 communicate with the fragrance outlet 64 of each fragrance chamber 28. The fragrance passage 70 has a taper portion that a diameter is reduced as it goes to a front side, and is formed in a shape of straight pipe in its front portion.

Furthermore, a center axis 72 that is a coupling portion of respective partitions 26 is formed in a shape of a hexagon prism, and projected from the partition wall 20 such that a tip end portion thereof is extended in the fragrance passage 70. The tip end portion of the center axis 72 is formed as a tapered shape that notches each having a shape of groove are formed on an outer periphery surface, and functions as a guide portion that guides, in a direction toward the emission port 68, a fragrance that is discharged from a fragrance outlet 64 of each fragrance chamber 28. Accordingly, a back flow of the fragrance and permeation of the fragrance into other fragrance chambers 28 can be prevented.

Furthermore, an auxiliary airflow source 74 is provided in the partition wall 20. The auxiliary airflow source 74 is provided separately from the airflow source 32 and independently from respective fragrance chambers 28, and is used for acceleration of the fragrance that is sent to the fragrance passage 70 from respective fragrance chambers 28, concentration adjustment of a fragrance component, deodorization, etc. In this embodiment, as the auxiliary airflow source 74, an article similar to the airflow source 32, that is, an article that comprises a diaphragm 38 adhered with a piezoelectric device 36 and generates an airflow by vibrating the diaphragm 38 at a high speed when a high frequency alternating voltage is applied to the piezoelectric device 36 is used. As shown in FIG. 5, an operation noise suppressing portion 48 is properly provided also in the rear side of this auxiliary airflow source 74, and an outside air inlet 52 of the operation noise suppressing portion 48 is communicated with the outside of the housing 12 via an air passage 56 formed in the partition wall 20, the control board room 24 and the outside air suction port 58 formed on the rear wall 18.

Furthermore, within the center axis 72, there is formed with an auxiliary passage 76 that becomes a passage of air (odorless air) discharged from a nozzle 34 of the auxiliary airflow source 74. The auxiliary passage 76 is a penetrating hole that makes the nozzle 34 of the auxiliary airflow source 74 and the fragrance passage 70 communicate with each other in a straight line manner, and is linearly extended up to the emission port 68 via the fragrance passage 70. A diameter of the auxiliary passage 76 is 0.8 mm, for example. If the auxiliary airflow source 74 is operated, the odorless air is discharged from the nozzle 34 of the auxiliary airflow source 74 into the auxiliary passage 76. The odorless air flows straight up to the emission port 68 without moving in a complex path, and accordingly, the odorless air is vigorously emitted from the emission port 68 without generating a drop of the pressure.

Furthermore, a screw hole 80 for attaching the tripod 102 is formed in a proper position of the housing 12. The screw hole 80 is formed on the side wall 14 around the control board room 24, in this embodiment. Furthermore, the standard of the screw hole 80 should suit a tripod for cameras. Since the standard of the screw of the tripod for cameras is unified by the global standard (¼ inch-20 UNC), if the standard of the screw hole 80 is fitted to the global standard, it is possible to use the tripod for the cameras around the world as the tripod 102 for the olfactory display 10 with no change, and thus, it is convenient.

As mentioned above, the olfactory display 10 having such the structure presents to the user a content that is presented by a personal computer or the like and includes an image and sound by adding a fragrance to the content. For example, in accordance with a scene change of a video content, a fragrance of vanilla can be emitted in a scene that a vanilla ice cream is eaten, and a fragrance of the sea can be emitted in a scene of the beach.

Specifically, the control board 22 of the olfactory display 10 applies the alternating voltage to the piezoelectric device 36 of the airflow source 32 corresponding to the fragrance chamber 28 that accommodates a target fragrance source 30 according to an instruction signal that is sent from the cooperating personal computer etc. and a control signal from the controller 300. Then, the diaphragm 38 is bent and vibrated at a high speed, and therefore, the air is sucked-in via the outside air suction port 58, the air passage 56, the operation noise suppressing portion 48, etc. into the airflow source 32, and the air at a high-speed and a high-pressure is sent into the fragrance chamber 28 from the nozzle 34 of the airflow source 32. A gas-like fragrance component volatilized from the fragrance source 30 is included in the air in the fragrance chamber 28, and the air including the fragrance component (fragrance) is discharged into the fragrance passage 70 from the fragrance outlet 64.

Furthermore, the control board 22 makes the auxiliary airflow source 74 operate according to an instruction signal that is sent from the cooperating personal computer etc. and a control signal from the controller 300. That is, the alternating voltage is also applied to the piezoelectric device 36 of the auxiliary airflow source 74. Accordingly, the odorless air that is discharged from the nozzle 34 of the auxiliary airflow source 74 goes direct to the emission port 68 through the inside of the auxiliary passage 76 in a shape of a straight line. The fragrance that is discharged from the fragrance outlet 64 into the fragrance passage 70 joins with the odorless air that is discharged from the auxiliary airflow source 74 within the fragrance passage 70 to be carried by the odorless air and accelerated toward the fragrance emission direction, and vigorously emitted from the emission port 68 with the straightness and without most time delay to the instruction signal from an outside such as a personal computer. Then, if the application of the alternating voltage to the piezoelectric devices 36 of the airflow source 32 and the auxiliary airflow source 74 is stopped, the emission of the fragrance from the emission port 68 is also stopped immediately.

At this time, since the piezoelectric type airflow source 32 and auxiliary airflow source 74 are used, the start and stop of the emission of the fragrance is performed with excellent responsiveness (that is, a precise temporal control is possible), and in addition thereto, continuous presentation of a constant fragrance not being pulsatile is also possible. Furthermore, since the auxiliary airflow source 74 is provided, even when decreased pressure arises in the fragrance passage 70 with only the airflow source 32, it is possible to appropriately accelerate the fragrance that is discharged from the fragrance chamber 28 to the fragrance emission direction, thereby to maintain or improve the emission performance of the fragrance. That is, the fragrance is vigorously emitted from the emission port 68 with directivity, and therefore, it is possible to present the fragrance in a very spatially restricted range (that is, only near a face of the user). Furthermore, adhesion (lingering fragrance) of the fragrance component in the fragrance passage 70 is also prevented.

In addition, if the fragrance component that is presented is volatilized or diluted by emitting only the odorless air by continuing operating the auxiliary airflow source 74 after stopping the airflow source 32 (after presentation of fragrance), quicker deodorization will be attained as compared with performing free diffusion of the fragrance component as it is.

Furthermore, in this embodiment, six (6) fragrance chambers 28 are provided, and the fragrance is emitted from a single emission port 68 via the fragrance passage 70. Therefore, it is, of course, possible to present six (6) kinds of fragrances individually, and by making the airflow sources 32 of respective fragrance chambers 28 operate simultaneously or a time-shared manner, the fragrances can be presented while being mixed. On the assumption that the fragrance sources 30 accommodated in the fragrance chambers 28 are A, B, C, D, E and F, for example, a number of kinds of fragrances can be presented by mixing the fragrances such as "A+B, A+C, --, E+F, --, B+C+D+E+F, A+B+C+D+E+F". Furthermore, by adjusting a Duty ratio of an input signal of each airflow source 32, it is possible to suitably change a ratio that the fragrances are mixed.

In this embodiment, as mentioned above, it is possible to adjust the concentration of the fragrance component by operating the adjustment knob 300a of the controller 300. Specifically, by alternately operating the airflow source 32 that functions as a fragrance emission portion and the auxiliary airflow source 74 that functions as a first air emission portion, and by controlling a time to be operated (hereinafter, called "operating time period") and a time to be stopped (hereinafter, called "stopping time period"), the mixing ratio of the fragrance from the fragrance chamber 28 and the odorless air from the auxiliary airflow source 74 can be adjusted.

In the following, a method of adjusting (controlling) the concentration of the fragrance component will be described. As a method of controlling the concentration of the fragrance component, a method (1) that the fragrance and the odorless air are alternately emitted while changing a time period that makes the fragrance and the odorless air emit, a method (2) that the fragrance and the odorless air are alternately emitted for a predetermined time period while changing the number of times emitting the fragrance and the odorless air, and a method (3) that the fragrance and the odorless air are alternately emitted while changing an amount that the fragrance is emitted (emission amount), for example.

Figure 7:
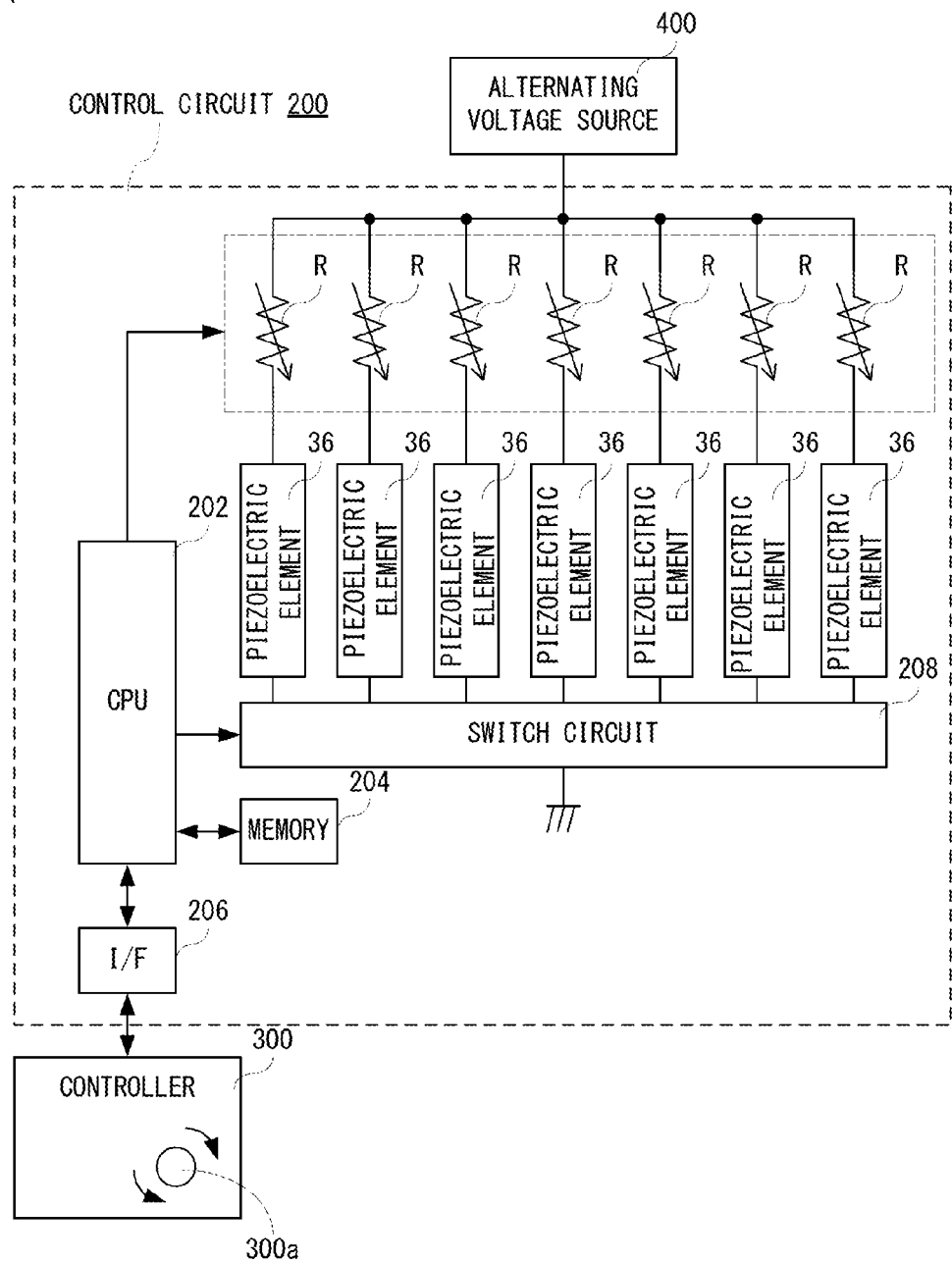
FIG. 7 is a circuit diagram showing an example of a control circuit mounted on a control board shown in FIG. 4.

An example of the control circuit 200 for realizing the method (1) to the method (3) is shown in FIG. 7, for example. This control circuit 200 is formed on the control board 22. As shown in FIG. 7, the control circuit 200 includes a CPU 202, and the CPU 202 is connected with a memory 204. The memory 204 is a rewritable storage medium such as a flash memory or RAM. Furthermore, an interface (I/F) 206 is connected to the CPU 202, and the controller 300 is connected to this I/F 206. Furthermore, a switch circuit 208 is connected to the CPU 202. This switch circuit 208 is connected with one ends of seven (7) piezoelectric devices 36 included in respective six (6) airflow sources 32 and one (1) auxiliary airflow source 74. Each of other ends of these piezoelectric devices 36 is connected, via a variable resistor R, to an alternating voltage source 400 provided outside the control circuit 200.

In addition, a host computer is communicably connected to the CPU 202 via the I/F 206 or another I/F.

The switch circuit 208 includes even (7) switching elements (FET, for example), for example, and is provided between each piezoelectric device 36 and the ground, respectively. According to a control signal from the controller 300, the CPU 202 controls a time to turn on/off each switching element, or controls (changes) a resistance value of each variable resistor R, or controls those both. That is, at least one of operating time periods of the airflow source 32 and the auxiliary airflow source 74 and magnitudes of amplitudes of the piezoelectric devices 36 included in the airflow source 32 and the auxiliary airflow source 74 are controlled.

Furthermore, information (fragrance source information) about the fragrance source 30 that is put into each fragrance chamber 28 is registered in the host computer by the user, and the fragrance source information is stored (preserved) in an internal memory (HDD, flash memory, etc.) of the host computer. Therefore, information of the fragrance to be emitted, that is, the airflow source 32 (piezoelectric device 36) provided in the fragrance chamber 28 into which the fragrance source 30 of the fragrance concerned is put is included in an instruction signal that is input to the olfactory display 10 (CPU 202) from the host computer.

Furthermore, a control signal for controlling (adjusting) the concentration of the fragrance component by the controller 300 is input to the control circuit 200 shown in FIG. 7. For example, a control signal for linearly changing the concentration according to a movement of the adjustment knob 300a of the controller is input to the CPU 202 (olfactory display 10), and according to the control signal, it is possible to linearly change the concentration of the fragrance component to be emitted from the olfactory display 10. However, since it is difficult for human sense of smell to recognize a small change of the concentration, the concentration may be changed in stages (stepwise). In this embodiment, for simplifying, a case where the concentration is adjusted (controlled) in three (3) stages (high, normal (medium degree), and low) will be described. If the adjustment knob 300a provided in the controller 300 is turned to the left most, for example, a control signal for making the concentration low is input to the CPU 202. Furthermore, if the adjustment knob 300a provided in the controller 300 is turned to the right most, a control signal for making the concentration high is input to the CPU 202. Then, if the adjustment knob 300a provided in the controller 300 is set at a position (hereinafter, called "intermediate position") between a position turned to the left most and a position turned to the right most, a control signal for making the concentration set normal (medium degree) is input to the CPU 202.

In a case of the method (1), during a fragrance presentation time period, the piezoelectric devices 36 of respective airflow sources (32, 74) are driven and stopped such that an operating time period of the airflow source 32 provided in the fragrance chamber 28 into which the fragrance source 30 of the fragrance to be presented and an operating time period of the auxiliary airflow source 74 are reversed. However, in the method (1) (also in the method (2)), the alternating voltage that a peak value is constant is applied to each piezoelectric device 36. Specifically, the alternating voltage form the alternating voltage source 400 is stepped-down by each variable resistor R, and then, a stepped-down alternating voltage (frequency of 26 kHz, 19.5 Vp-p, for example) is applied to each piezoelectric device 36.

In addition, the fragrance presentation time period is a time period designated in an instruction signal when the instruction signal that instructs to present the fragrance is input from the host computer.

In FIG. 8(A) and FIG. 8(B), examples (changes of operation and stop in a time series) for controlling the operation of the airflow source 32 and the auxiliary airflow source 74 when the control signal in order to set the concentration of the fragrance component normal (medium degree) is input to the CPU 202 from the controller 300 by setting the adjustment knob 300a at the intermediate position are shown. In FIG. 9(A) and FIG. 9(B), examples for controlling the operation of the airflow source 32 and the auxiliary airflow source 74 when the control signal in order to set the concentration of the fragrance component high is input to the CPU 202 from the controller 300 by turning the adjustment knob 300a to the right most are shown. In FIG. 10(A) and FIG. 10(B), examples for controlling the operation of the airflow source 32 and the auxiliary airflow source 74 when the control signal in order to set the concentration of the fragrance component low is input to the CPU 202 from the controller 300 by turning the adjustment knob 300a to the left most are shown.

However, the airflow source 32 in FIG. 8(A), FIG. 9(A) and FIG. 10(A) is the airflow source 32 that is provided in the fragrance chamber 28 into which the fragrance source 30 designated by the host computer, that is, the fragrance source 30 of the fragrance to be presented is put.

As mentioned above, in the method (1), the operating time period of the airflow source 32 and the operating time period of the auxiliary airflow source 74 are reversed, and the airflow source 32 and the auxiliary airflow source 74 are alternately operated.

Furthermore, in this embodiment, a single operating time period of the airflow source 32 is determined according to the concentration of the fragrance component. As mentioned above, in order to change the concentration in three (3) stages, in this embodiment, a single operating time period of the airflow source 32 is changed according to a case where the adjustment knob 300a is turned to the left most, a case where the adjustment knob 300a is set at the intermediate position and a case where the adjustment knob 300a is turned to the right most.

On the basis of the operating time period (1 second, for example) when the concentration of the fragrance component is normal (medium degree), for example, the operating time period when the concentration of the fragrance component is high is 1.5 times (1.5 seconds) and the operating time period when the concentration of the fragrance component is low is 0.5 times (0.5 seconds). Here, a cycle that controls the operation of the airflow source 32 is 2 seconds, for example. Numeral values about the operating time periods and the cycles according to the concentrations are stored in the memory 204, and the CPU 202 controls turning on/off of the switching elements provided in the switch circuit 208 according to these numeral values when the control signal is received from the controller 300.

Returning to FIG. 8(A) and FIG. 8(B), since a single operating time period of the airflow source 32 is 1 second and the cycle that controls the operation thereof is 2 seconds when the concentration of the fragrance component is normal, a single operating time period of the auxiliary airflow source 74 is set as 1 second. That is, the single operating time period of the airflow source 32 and the single operating time period of the auxiliary airflow source 74 are set as the same length.

In addition, in FIG. 8(A) and FIG. 8(B) (in also FIG. 9-FIG. 13), the operating time period is indicated as "H" (high level) and the stopping time period is indicated as "L" (low level); however, it should be noted that these mean levels of pulses that the CPU 202 applies to the switching elements such as FETs. That is, in this embodiment, when a pulse is the high level, a switching element is turned on, and when a pulse is the low level, a switching element is turned off.

Furthermore, since a single operating time period of the airflow source 32 is 1.5 seconds and the cycle that controls the operation thereof is 2 seconds when the concentration of the fragrance component is high as shown in FIG. 9(A) and FIG. 9(B), a single operating time period of the auxiliary airflow source 74 is set as 0.5 seconds. That is, the single operating time period of the airflow source 32 is set to three (3) times the length of the single operating time period of the auxiliary airflow source 74. Therefore, the concentration of the fragrance component is made higher than a case where the concentration is normal.

Furthermore, since a single operating time period of the airflow source 32 is 0.5 seconds and the cycle that controls the operation thereof is 2 seconds when the concentration of the fragrance component is low as shown in FIG. 10(A) and FIG. 10(B), a single operating time period of the auxiliary airflow source 74 is set as 1.5 seconds. That is, the single operating time period of the airflow source 32 is set to one-third the length of the single operating time period of the auxiliary airflow source 74. Therefore, the concentration of the fragrance component is made lower than a case where the concentration is normal.

Figure 8:
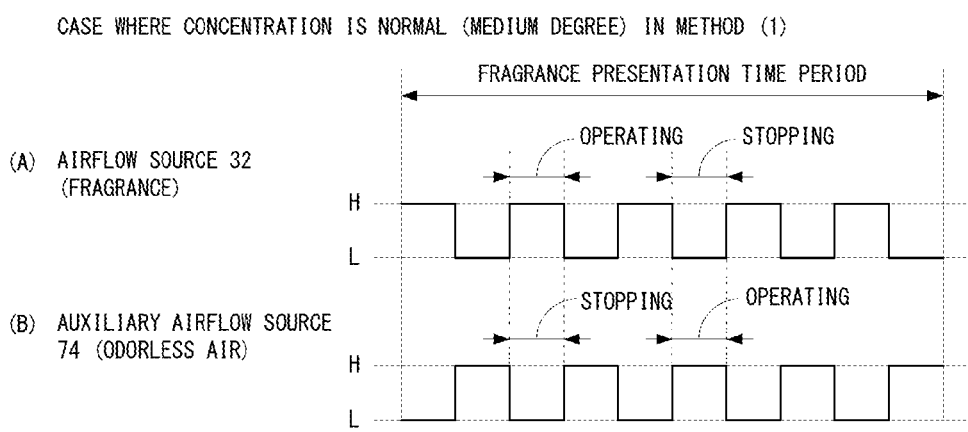
FIG. 8 is an illustration view showing an example of a method (1) for adjusting a concentration of a fragrance component emitted from the olfactory display of FIG. 1.
Figure 9:
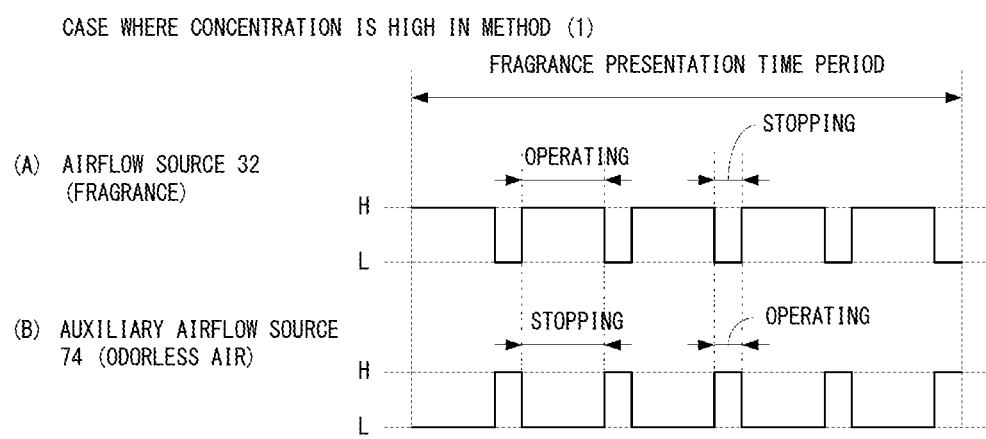
FIG. 9 is an illustration view showing another example of the method (1) for adjusting the concentration of the fragrance component emitted from the olfactory display of FIG. 1.
Figure 10:
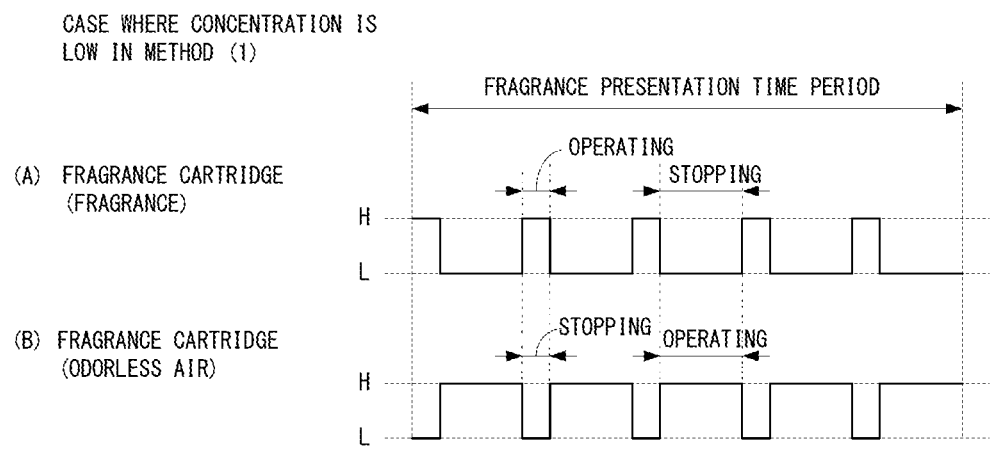
FIG. 10 is an illustration view showing the other example of the method (1) for adjusting the concentration of the fragrance component emitted from the olfactory display of FIG. 1.
Figure 11:
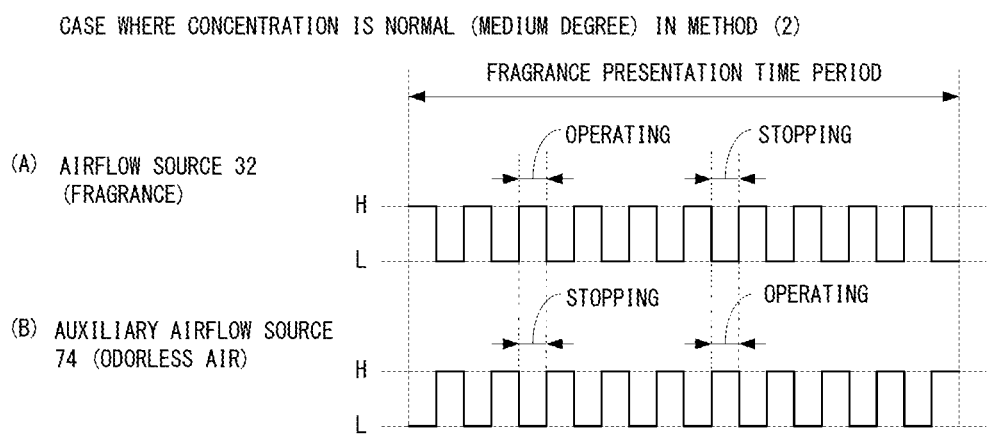
FIG. 11 is an illustration view showing an example of a method (2) for adjusting a concentration of a fragrance component emitted from the olfactory display of FIG. 1.
Figure 12:
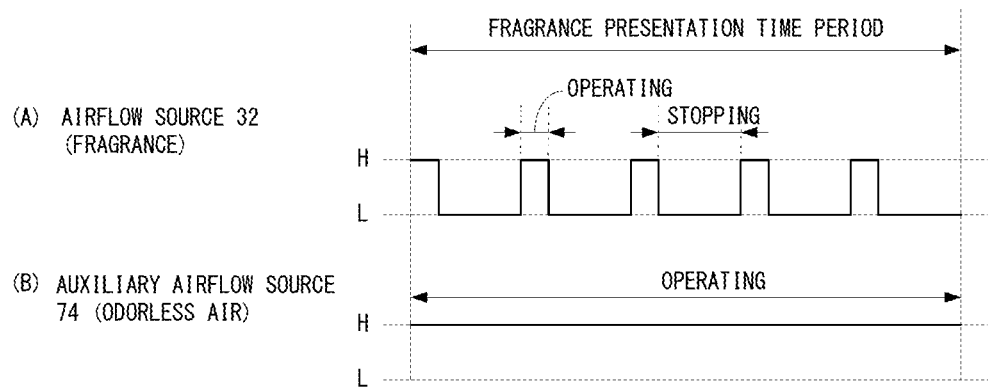
FIG. 12 is an illustration view showing a modified example of the method (1) and the method (2) for adjusting the concentration of the fragrance component emitted from the olfactory display of FIG. 1.
Figure 13:
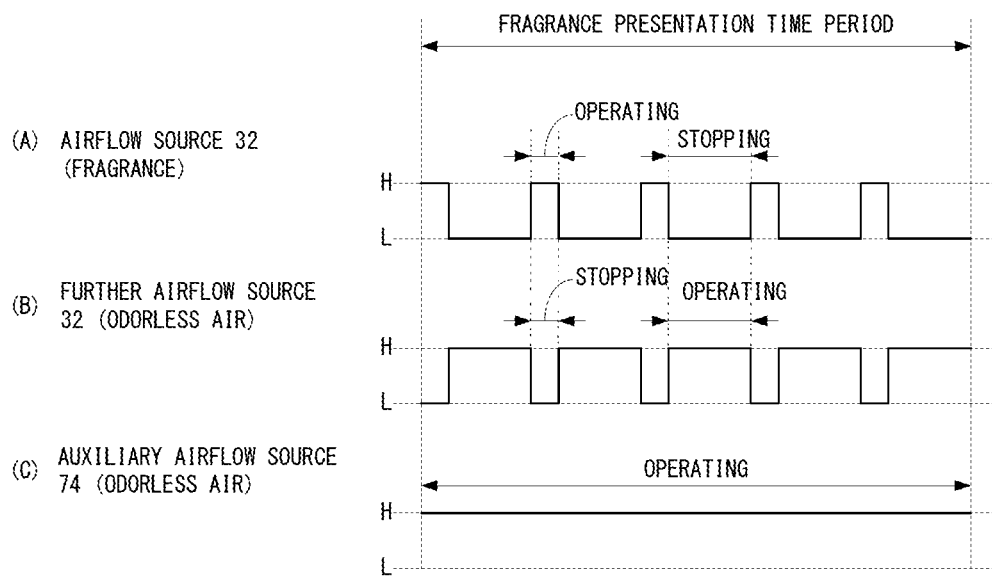
FIG. 13 is an illustration view showing another example of the method (1) and the method (2) for adjusting the concentration of the fragrance component emitted from the olfactory display of FIG. 1.

In the case of the method (1) shown in above-mentioned FIG. 8-FIG. 10, a single operating time period of the airflow source 32 according to the concentration is determined in advance, but it does not need to be limited to this. For example, in the case of the method (2), it is possible to adjust the concentration by the number of operating times (frequency) that the airflow source 32 and the auxiliary airflow source 74 are operated while setting the single operating time period of the airflow source 32 as a predetermined length. Therefore, in the method (2), information of this predetermined length of the operating time period is stored in the memory 204.

In such a case, a calculation is made such that the number of operating times of the airflow source 32 and the auxiliary airflow source 74 in the fragrance presentation time period become equal to each other according to the concentration of the fragrance component. However, on the assumption of definition that the concentration of the fragrance component is 100 percent in a case where the fragrance is continued to be presented in the fragrance presentation time period, an entire operating time period of the airflow source 32 is set to 50 percent length of the fragrance presentation time period when the concentration of the fragrance component is normal, an entire operating time period of the airflow source 32 is set to 75 percent length of the fragrance presentation time period when the concentration of the fragrance component is high, and an entire operating time period of the airflow source 32 is set to 25 percent length of the fragrance presentation time period when the concentration of the fragrance component is low.

When the fragrance presentation time period is 10 seconds and the concentration of the fragrance component is normal, for example, 5 seconds being a half of the presentation time period is assigned as an entire time period that the fragrance is emitted, and 5 seconds being the remaining half is assigned as an entire time period that the odorless air is to be emitted. Here, if the single operating time period of the airflow source 32 is set as 0.5 seconds (the cycle is 1 second), as shown in FIG. 11(A) and FIG. 11(B), the airflow source 32 is equally operated ten (10) times, and the auxiliary airflow source 74 is equally operated ten (10) times by reversing the operating time period and the stopping time period.

Furthermore, when the concentration is low, the fragrance is emitted for 2.5 seconds during the fragrance presentation time period, and the odorless air is emitted for the remaining 7.5 seconds. In such a case, the airflow source 32 is operated equally five (5) times like the case shown in FIG. 10(A) and FIG. 10(B). That is, in this case, since the auxiliary airflow source 74 is operated equally five (5) times when the airflow source 32 is stopped, the operating time period of the auxiliary airflow source 74 is set as 1.5 seconds.

When the concentration of the fragrance component is high, the fragrance is emitted for 7.5 seconds during the fragrance presentation time period, and the odorless air is emitted for the remaining 2.5 seconds. In such a case, if the single operating time period of the airflow source 32 is left 0.5 seconds, the fragrance is emitted fifteen (15) times. Then, if the odorless air is emitted by the same number of times, the single operating time period of the auxiliary airflow source 74 will be about 0.167 seconds. It is empirically acquired through the experiment etc. that it is necessary to operate the airflow source 32 and the auxiliary airflow source 74 by the length of 0.5 seconds or more in order to stably emit the fragrance and the odorless air. Therefore, in order to make the single operating time period of the auxiliary airflow source 74 up to 0.5 seconds or more, it is necessary to divide 2.5 seconds that is an entire time period that the airflow source 32 is operated into at most five (5) times. Furthermore, in order to alternately operate the airflow source 32 and the auxiliary airflow source 74, it is necessary to make the airflow source 32 operate five (5) times. Accordingly, the single operating time period of the airflow source 32 is changed to 1.5 seconds. Therefore, the operation of the airflow source 32 and the auxiliary airflow source 74 is controlled like the case shown in FIG. 9(A) and FIG. 9(B).

Even if the number of operating times of the airflow source 32 and the auxiliary airflow source 74 is thus calculated while setting the single operating time period of the airflow source 32 to the predetermined length, it is possible to adjust (control) the concentration of the fragrance component. However, when the operating time period calculated for the airflow source 32 and the auxiliary airflow source 74 also becomes less than 0.5 seconds in a case where the concentration of the fragrance component is adjusted (controlled) in four (4) or more stages, it is necessary, as mentioned above, to change the operating time period and the number of operating times such that the operating time period becomes 0.5 seconds or more.

As mentioned above, although the airflow source 32 and the auxiliary airflow source 74 are operated by turns in FIG. 8-FIG. 11, these may be operated simultaneously. When a ratio to mix odorless air is equal to a ratio to mix the fragrance, for example, the airflow source 32 and the auxiliary airflow source 74 are operated and stopped at the same timings. Furthermore, when a ratio to mix odorless air is different from a ratio to mix the fragrance, the airflow source 32 and the auxiliary airflow source 74 are operated at the same timings but stopped at different timings. Even in such a case, since the fragrance that is discharged into the fragrance passage 70 from the fragrance outlet 64 joins to the odorless air that is discharged from the auxiliary airflow source 74 within the fragrance passage 70, the concentration of the fragrance component can be adjusted according to a ratio discharging (emitting) the fragrance and the odorless air. This is true about the case of the method (3) shown in FIG. 15 describe later.

In addition, although the concentration is adjusted by alternately operating the airflow source 32 and the auxiliary airflow source 74 to change the ratio of emissions of the fragrance and odorless air in a case shown in FIG. 8-FIG. 11, it is possible to adjust the concentration of the fragrance component only by changing the operating time period and the stopping time period of the airflow source 32.

Another example in a case where the concentration of the fragrance component is low is shown in FIG. 12(A) and FIG. 12(B), for example. In such a case, as shown in FIG. 12(A), the airflow source 32 is controlled like the case shown in FIG. 11(A). On the other hand, as shown in FIG. 12(B), the auxiliary airflow source 74 is always operated in the fragrance presentation time period.

Furthermore, although illustration is omitted, the stopping time period of the airflow source 32 and the operating time period of the auxiliary airflow source 74 are set to the same length while setting the operating time period of the airflow source 32 and the stopping time period of the auxiliary airflow source 74 to the same length, it does not need to be limited to this. For example, the operating time period of the auxiliary airflow source 74 may be set short so as to include a part of the stopping time period of the airflow source 32, or may be set so as to include a whole of the stopping time period of the airflow source 32 (except for the same length) is included.

Here, as mentioned above, in order to stably emit the fragrance and the odorless air, it is necessary to operate the airflow source 32 and the auxiliary airflow source 74 by the length of 0.5 seconds or more in this embodiment. Then, it is impossible to present the fragrance having further lower concentration only by operating the auxiliary airflow source 74 and the airflow source 32 by turns, or by always operating the auxiliary airflow source 74.

Therefore, in this embodiment, only a granular body such as a porous body, a non-porous body, etc. that the fragrance component is not added is accommodated in the fragrance chamber 28, or a fragrance chamber 28 is made as a vacant room containing nothing, odorless air is further emitted from the fragrance chamber 28.

As an example, as shown in FIG. 13(A) and FIG. 13(B), the airflow source 32 of the fragrance chamber 28 into which the fragrance source 30 is put and a further airflow source 32 of the fragrance chamber 28 into which the fragrance source 30 etc. is not put are operated by turns during the fragrance presentation time period like the case shown in FIG. 10(A) and FIG. 10(B). In this case, the further airflow source 32 functions as a second air emitting portion. Furthermore, as shown in FIG. 13(C), in the fragrance presentation time period, the auxiliary airflow source 74 is always operated. However, control of the further airflow source 32 and the auxiliary airflow source 74 may be reversed.

In addition, the auxiliary airflow source 74 may be controlled like the further airflow source 32 shown in FIG. 13(B).

Furthermore, two or more fragrance chambers into each of which the fragrance source 30 etc. is not put, and one or two or more of the airflow sources 32 provided in these fragrance chambers 28 may be simultaneously controlled like the case shown in FIG. 13(B). Then, it is possible to make the concentration of the fragrance component low in a plurality of stages.

In addition, although it is matter of course, if the fragrance source 30 of the same fragrance is put into each of a plurality of fragrance chambers 28, and if the airflow sources 32 of the plurality of fragrance chambers 28 are operated simultaneously, it is possible to make the concentration of the fragrance component higher than a case where the airflow source 32 of only one fragrance chamber 28 out of them is operated.

Next, a case where the above-mentioned method (3) is realized will be described. In the case of the method (3), if a control signal of the controller 300 is input to the CPU 202, the CPU 202 changes a voltage value of the alternating voltage that is applied from the alternating voltage source 400 to the piezoelectric device 36 of the airflow source 32 by changing the resistance value of the variable resistor R. It is possible to change the voltage value of the alternating voltage between 5 Vp-p and 30 Vp-p. However, a frequency is constant at 26 kHz.

In addition, in this embodiment, the voltage value of the alternating voltage that is applied to the piezoelectric device 36 (the piezoelectric device 36 at the right end in the example of the control circuit 200 shown in FIG. 7) of the auxiliary airflow source 74 is constant (frequency of 26 kHz, 19.5 Vp-p, for example).

Figure 14:
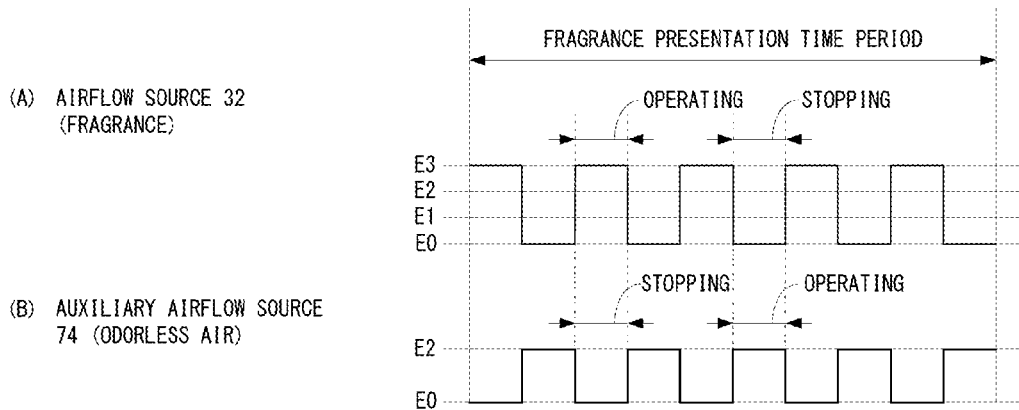
FIG. 14 is an illustration view showing an example of a method (3) for adjusting a concentration of a fragrance component emitted from the olfactory display of FIG. 1.

As mentioned above, since the voltage value of the alternating voltage is changed in the method (3), an amplitude (vibration magnitude) of the piezoelectric device 36 that is provided in the airflow source 32 is changed, and an amount of the fragrance emitted at a time increases or decreases according to the change of the amplitude. Furthermore, in this method (3), since the concentration of the fragrance component is changed by the voltage value of the alternating voltage, as shown in FIG. 14(A) and FIG. 14(B), the CPU 202 controls turning on/off of the switching element included in the switch circuit 208 such that the operating time period and the stopping time period of the airflow source 32 become the same length (here, 1 second). The information about this operating time period (and stopping time period) is stored in the memory 204. That is, the CPU 202 inputs a pulse having a waveform as shown in FIG. 8(A) to the switching element for driving/stopping the piezoelectric device 36 of the airflow source 32. Furthermore, since the auxiliary airflow source 74 is alternately operated with the airflow source 32, the CPU 202 inputs a pulse having a waveform as shown in FIG. 8(B) to the switching element for driving/stopping the piezoelectric device 36 of the auxiliary airflow source 74.

When setting the concentration of the fragrance component high in the method (3), as shown in FIG. 14(A) and FIG. 14(B), the alternating voltage is applied to the piezoelectric device 36 of the airflow source 32 and the auxiliary airflow source 74. In addition, the alternating voltage is E3 (30 Vp-p)>E2 (19.5 Vp-p)>E1 (10 Vp-p)>E0 (0V). Also in FIG. 14(A) and FIG. 14(B), for simplifying, a case where the concentration of the fragrance component is changed in three (3) stages is shown.

As shown in FIG. 14(A), when the concentration of the fragrance component is high, the alternating voltage of E3 is applied to the piezoelectric device 36 of the airflow source 32. Although illustration is omitted, when the concentration of the fragrance component is normal (medium degree), the alternating voltage of E2 is applied to the piezoelectric device 36 of the airflow source 32. Furthermore, when the concentration of the fragrance component is low, the alternating voltage of E1 is applied to the piezoelectric device 36 of the airflow source 32. Furthermore, as shown in FIG. 14(B), the alternating voltage of E2 is applied to the piezoelectric device 36 of the auxiliary airflow source 74 so as to be alternately operated with the airflow source 32 in the fragrance presentation time period.

However, as shown in FIG. 12(B), the auxiliary airflow source 74 may be always operated during the fragrance presentation time period. Furthermore, as shown in FIG. 13(B) and FIG. 13(C), the auxiliary airflow source 74 may be operated together with the further airflow source 32 of the fragrance chamber 28 into which the odorless air is put.

In the above-mentioned embodiment, the lengths of the operating time period and the stopping time period of the airflow source 32 and the auxiliary airflow source 74 are changed, or the number of operating times of the airflow source 32 and the auxiliary airflow source 74 are calculated while setting the operating time period of the airflow source 32 at the predetermined length, or the voltage value of the alternating voltage to be applied to the piezoelectric device 36 of the airflow source 32 is changed, whereby the concentration of the fragrance component is controlled; however, it does not need to be limited to this.

For example, the concentration of the fragrance component may be controlled by changing the lengths of the operating time period and the stopping time period of the airflow source 32 and the auxiliary airflow source 74, and by changing the voltage value of the alternating voltage that is applied to the piezoelectric device 36 of the airflow source 32. That is, the method (1) and the method (3) may be combined with each other. Furthermore, the concentration of the fragrance component may be controlled by calculating the number of operating times of the airflow source 32 and the auxiliary airflow source 74 while setting the operating time period of the airflow source 32 at the predetermined length, and by changing the voltage value of the alternating voltage that is applied to the piezoelectric device 36 of the airflow source 32. That is, the method (2) and the method (3) may be combined with each other.

Furthermore, although the concentration is not adjusted in the fragrance presentation time period in the above-mentioned embodiments, it is possible to adjust the concentration of the fragrance component also in the fragrance presentation time period concerned by changing the adjustment knob 300a.

According to this embodiment, since the fragrance and the odorless air are emitted alternately or simultaneously, it is possible to uniformly present the fragrance that the concentration is controlled according to the mixing ratio of the fragrance and the odorless air.

Furthermore, according to this embodiment, since the odorless air can be emitted from the fragrance chamber by putting the odorless air into the fragrance chamber, control of detailed concentration becomes possible by using properly with the odorless air that is emitted by the auxiliary airflow source, or using the odorless air simultaneously.

Furthermore, according to this embodiment, it is possible to easily control the concentration of the fragrance component because the concentration of the fragrance component is controlled only by changing the lengths of the operating time period and the stopping time period of the airflow source and an auxiliary airflow source, or the number of operating times of the airflow source and the auxiliary airflow source while setting the operating time period of the airflow source at the predetermined length, or the voltage value of the alternating voltage that is applied to the piezoelectric device of the airflow source.

In addition, in this embodiment, although discharging performance (static pressure generation ability) of the airflow source and discharging performance of the auxiliary airflow source may be made comparable, the discharging performance of the auxiliary airflow source may be made higher than the discharging performance of the airflow source. By thus making the discharging performance of the auxiliary airflow source higher than the discharging performance of the airflow source, it is possible to make the concentration lower in a case where the concentration of the fragrance component is reduced by the odorless air that is emitted by the auxiliary airflow source in comparison with a case where the concentration of the fragrance component is reduced by the odorless air that is put into the fragrance chamber.

Furthermore, although the control signal is input from the controller 300 in this embodiment, the host computer may input the instruction signal and the control signal.

Furthermore, it should not be limited to the structure of the olfactory display shown in this embodiment. Various structures can be adopted only if the fragrance and the odorless air can be emitted from the same emission port. For example, the fragrance chamber may be attached with a cartridge that a fragrance source is enclosed. Furthermore, it is unnecessary to limit a shape of the housing to a shape of a hexagon prism, the shape may be changed to a proper shape such as a cube, a rectangular parallelepiped, a polygonal prism, a cylinder, etc. according to the number of the fragrance chambers, etc. Furthermore, it is possible to properly change the number of sheets of the partition dividing the inside of the housing and a shape of the center axis according to the number of the fragrance chambers to be formed, etc.

Figure 15:
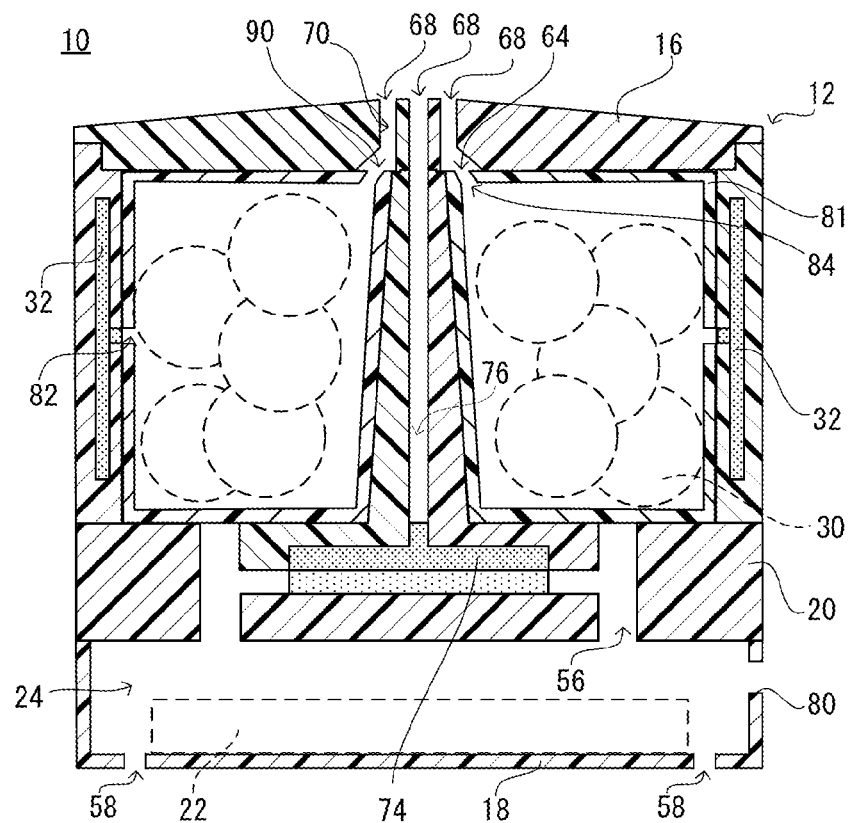
FIG. 15 is an illustration view roughly showing internal structure of an olfactory display that is a further embodiment according to the present invention while viewed from a front direction.

FIG. 15 shows a schematic view of internal structure viewed from a side direction of an olfactory display 10 according to a further embodiment. As shown in FIG. 15, in the olfactory display 10 of the further embodiment, each fragrance chamber 28 is attached with a fragrance cartridge 81. A fragrance source 30 is enclosed in this fragrance cartridge 81. In addition, only a single fragrance cartridge 81 may be attached. Furthermore, an odorless air may be enclosed in the fragrance cartridge 81.

Furthermore, as shown in FIG. 15, a feed-in port 82 is provided in the fragrance cartridge 81, which is connected to the nozzle 34 of the airflow source 32. Therefore, the air discharged from the nozzle 34 is sent into the fragrance cartridge 81. Furthermore, a feed-out port 84 is provided in the fragrance cartridge 81, and the feed-out port 84 is coupled to the fragrance outlet 64. Therefore, the fragrance (odorless air) in the fragrance cartridge 81 is discharged into the fragrance passage 70 via the fragrance outlet 64 from the feed-out port 84.

Figure 16:
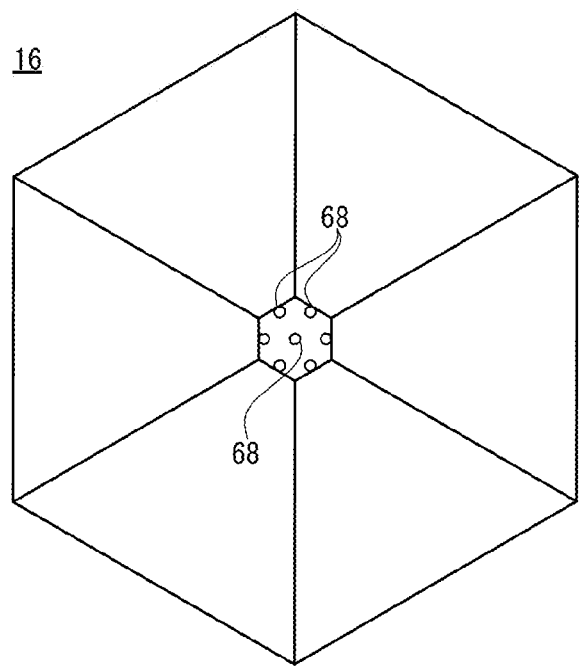
FIG. 16 is an illustration view showing an appearance of a front wall provided on the olfactory display of FIG. 15 while viewed from a front direction.

Furthermore, as shown in FIG. 15 and FIG. 16, in the olfactory display 10 of the further embodiment, a front wall 16 is formed in a shape of a hexagon plate, and a thickness thereof is thickened gradually toward a center portion from a peripheral portion. Seven (7) emission ports 68 are provided in a center portion at a front side of the front wall 16. These seven (7) emission ports 68 are collectively formed in near positions in the center portion at the front side of the front wall 16. Specifically, there are provided with six (6) emission ports 68 that are arranged in a shape of a circle, and one (1) emission port 68 is provided in a center portion of the circle. A distance between adjacent emission ports 68 is 2 mm, for example.

Figure 17:
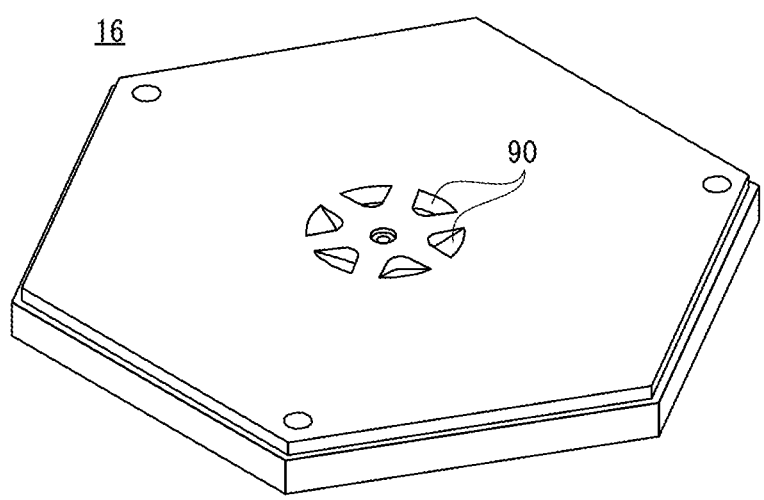
FIG. 17 is a perspective view showing a back side of the front wall of FIG. 16.

Each of the emission ports 68 that are arranged in a shape of the circle is communicated with the fragrance passage 70 of each fragrance chamber 28 via an individual communicating hole 90. That is, the fragrance that is discharged from the feed-out port 84 of the fragrance cartridge 81 is emitted from the individual emission port 68 through the individual communicating hole 90. The fragrance entrance portion (fragrance outlet 64) of each communicating hole 90 is formed slightly larger than the feed-out port 84 of the fragrance cartridge 81. Then, each communicating hole 90 is diameter-reduced in a shape of a taper from the fragrance outlet 64, and extended in a shape of a straight pipe toward the front. Accordingly, the fragrance (or the odorless air) that is discharged from the feed-out port 84 of the fragrance cartridge 81 is smoothly drawn to the emission port 68 via the communicating hole 90. Furthermore, the emission port 68 that is provided in the center portion of the six (6) emission ports 68 is linearly communicated with a nozzle of the auxiliary airflow source 74 via an auxiliary passage 76 (see FIG. 17).

Also in such an olfactory display 10 of the further embodiment, it is possible to make the fragrance and the odorless air properly emit from different emission ports 68, respectively by controlling the operation of the airflow source 32 and the auxiliary airflow source 74 by means of any one of the method (1) to the method (3) as mentioned above.

As mentioned above, since the seven (7) emission ports 68 are arranged in positions close to each other, the fragrance and the odorless air that are emitted from different emission ports 68 advance on an approximately the same course outside the housing 12 in a manner of straight line and join with each other outside the housing 12. Therefore, in such a case, it is possible to uniformly present the fragrance that the concentration is controlled according to the mixing ratio of the fragrance and the odorless air.

Furthermore, although a thing that a liquid aromatic material is soaked into a granular porous material is used as a solid-like fragrance source in the above-mentioned embodiments, it does not need to be limited to this. For example, it is possible to use as the solid-like fragrance source an article after dissolving the base material of a solid or gelatinous at the normal temperature to the liquid aromatic material, the liquid aromatic material is solidified or gelated by cooling at the normal temperature. However, it is preferable to use an article that the liquid aromatic material is soaked into the porous material as the solid-like fragrance source from a viewpoint that it can be manufactured simply and cheaply and that a supplement of liquid aromatic material can be performed.

The specific numerical values mentioned in this specification are only examples, and changeable properly in accordance with the change of product specifications.

DESCRIPTION OF NUMERALS

10—olfactory display
12—housing
22—control board
24—control board room
26—partition
28—fragrance chamber
30—fragrance source
32—airflow source
36—piezoelectric device
38—diaphragm
48—operation noise suppressing portion
62—air intake port
64—fragrance outlet
68—emission port
70—fragrance passage
74—auxiliary airflow source
81—fragrance cartridge
82—feed-in port
84—feed-out port
90—communicating hole
100—audio visual display
200—control circuit
208—switch circuit
300—controller
300a—adjustment knob
400—alternating voltage source

What we claimed is:

1. An olfactory display presenting a fragrance, comprising:
a housing having an emission port;
a fragrance emission portion that is provided in an inside of the housing and configured to emit a fragrance from the emission port;
a first air emission portion that is provided in the inside of the housing and configured to emit odorless air from the emission port; and
an emission control module configured to make the fragrance emission portion and the first air emission portion operate alternately or simultaneously.

2. The olfactory display according to claim 1, wherein the emission control module is configured to change a length of an operating time period that the fragrance emission portion is operated and a length of a stopping time period that the fragrance emission portion is stopped, and a length of an operating time period that the first air emission portion is operated and a length of a stopping time period that the first air emission portion is stopped.

3. The olfactory display according to claim 1, wherein the emission control module is configured to change an emission amount of the fragrance during the operating time period that the fragrance emission portion is operated.

4. The olfactory display according to claim 1, further comprising a second air emission portion that is provided in the inside of the housing and configured to emit odorless air from the emission port, the second air emission portion being different from the first air emission portion,
wherein the emission control module is configured to make the second air emission portion operate together with the first air emission portion or with being switched from the first air emission portion concerned.

5. The olfactory display according to claim 1, further comprising a calculation module configured to set the operating time period that the fragrance emission portion is operated to a predetermined time period, and calculate, according to the concentration of the fragrance to be presented, the number of operating times that the fragrance emission portion concerned and the first air emission portion concerned are operated during a fragrance presentation time period that presents the fragrance,
wherein the emission control module is configured to makes the fragrance emission portion and the first air emission portion operate alternately by the number of operating times calculated by the calculation module.

6. The olfactory display according to claim 2, wherein the emission control module is configured to change an emission amount of the fragrance during the operating time period that the fragrance emission portion is operated.

7. The olfactory display according to claim 2, further comprising a second air emission portion that is provided in the inside of the housing and configured to emit odorless air from the emission port, the second air emission portion being different from the first air emission portion, wherein the emission control module is configured to make the second air emission portion operate together with the first air emission portion or with being switched from the first air emission portion concerned.

8. The olfactory display according to claim 3, further comprising a second air emission portion that is provided in the inside of the housing and configured to emit odorless air from the emission port, the second air emission portion being different from the first air emission portion, wherein the emission control module is configured to make the second air emission portion operate together with the first air emission portion or with being switched from the first air emission portion concerned.

9. The olfactory display according to claim 2, further comprising a calculation module configured to set the operating time period that the fragrance emission portion is operated to a predetermined time period, and calculate, according to the concentration of the fragrance to be presented, the number of operating times that the fragrance emission portion concerned and the first air emission portion concerned are operated during a fragrance presentation time period that presents the fragrance, wherein the emission control module is configured to makes the fragrance emission portion and the first air emission portion operate alternately by the number of operating times calculated by the calculation module.

10. The olfactory display according to claim 3, further comprising a calculation module configured to set the operating time period that the fragrance emission portion is operated to a predetermined time period, and calculate, according to the concentration of the fragrance to be presented, the number of operating times that the fragrance emission portion concerned and the first air emission portion concerned are operated during a fragrance presentation time period that presents the fragrance, wherein the emission control module is configured to makes the fragrance emission portion and the first air emission portion operate alternately by the number of operating times calculated by the calculation module.

11. The olfactory display according to claim 4, further comprising a calculation module configured to set the operating time period that the fragrance emission portion is operated to a predetermined time period, and calculate, according to the concentration of the fragrance to be presented, the number of operating times that the fragrance emission portion concerned and the first air emission portion concerned are operated during a fragrance presentation time period that presents the fragrance, wherein the emission control module is configured to makes the fragrance emission portion and the first air emission portion operate alternately by the number of operating times calculated by the calculation module.

12. An olfactory display presenting a fragrance, comprising:

a housing having a plurality of emission ports that are arranged in positions close to each other;

a fragrance emission portion that is provided in an inside of the housing and configured to emit a fragrance from a first emission port out of the plurality of emission ports;

a first air emission portion that is provided in the inside of the housing and configured to emit odorless air from a second emission port out of the plurality of emission ports, the second emission port being different from the first emission port; and an emission control module configured to make the fragrance emission portion and the first air emission portion operate alternately or simultaneously.

* * * * *